United States Patent [19]

Pavlich

[11] Patent Number: 4,859,694
[45] Date of Patent: Aug. 22, 1989

[54] METHOD FOR TREATING HOOF THRUSH AND HOOF ROT

[76] Inventor: Frederick M. Pavlich, 300 Crestview Dr., Fox River Grove, Ill. 60021

[21] Appl. No.: 154,787

[22] Filed: Feb. 10, 1988

[51] Int. Cl.$^4$ ............................................ A61K 31/415
[52] U.S. Cl. ........................................ 514/398; 424/61
[58] Field of Search ............................ 424/61; 514/398

[56] References Cited

U.S. PATENT DOCUMENTS 3,961,068  6/1976  Maestrone et al. ................ 514/398
4,070,451  1/1978  Price .................................... 424/61

FOREIGN PATENT DOCUMENTS 0064830  11/1982  European Pat. Off. ............. 424/61

Primary Examiner—Frederick E. Waddell
Attorney, Agent, or Firm—Allegretti & Witcoff, Ltd.

[57] ABSTRACT

This invention relates to a new and unexpectedly effective method of treating and preventing the recurrence of thrush, a disease of the hoof and frog tissue, in horses. The method comprises administering a therapeutically effective amount of metronidazole in a carrier directly on a thrush infected area for a treatment period effective to cure the thrush infection. The method may also be applied to the treatment of the analogous hoof disease in sheep, goats and cattle known as hoof rot.

13 Claims, No Drawings

METHOD FOR TREATING HOOF THRUSH AND HOOF ROT

BACKGROUND OF THE INVENTION

A. Field of the Invention

This invention relates to a method of treating hoof thrush in horses and the analogous disease of hoof rot in sheep and cattle. Hoof thrush is a disease of the hoof and frog tissue in horses caused by a variety of pathogens, primarily *Spherophorus necrophorus*, an anaerobic bacterium. Hoof rot is the analogous hoof disease in sheep, goats and cattle also primarily caused by *Spherophorus necrophorus*. Merck Veterinary Manual, 6th Edition, Fraser, C. M., Ed. (1986) at pp. 983–84; Ensminger, M. E., *The stockman's Handbook*, 1st Ed., The Interstate Printers and Publishers (1955) at p.378–79; *The Sheepman's Production Handbook*, Scott, G. E., Ed., Abegg Printing (1970) at pp. 104–105. Most manure and dirt contains this bacterium and if allowed to pack into the foot and remain for very long, it will attack the hoof. Regular cleaning of the hoof prevents thrush from getting started by allowing air to reach the exposed area. Butler, D., *Principles and Practice of Horseshoeing*, Butler Publishing, (1974) at p. 176.

Thrush is common in horses and poses a constant problem for owners and grooms. Horses that are particularly susceptible are those that are confined for most of their day and not exercised to a reasonable degree. The predisposing causes of thrush are thus unhygienic conditions, dirty uncleaned feet and lack of frog pressure resulting from poor shoeing or poor foot trimming. Adams, O.R., *Lameness in Horses*, 2nd Ed., Lea & Febiger (1966) at p. 354. The diagnostic signs of thrush disease (and similarly of hoof rot disease) include: (1) a strong, unpleasant odor and an increased amount of moisture associated with the hoof and frog tissue; (2) a black discharge from the sulcae of the frog tissue; (3) a softening and destruction of the frog tissue (a "cheesy" appearance of the frog); and (4) lameness. Diagnosis of hoof thrush in horses is based primarily on the odor and physical characteristics of the black discharge in the sulci of the frog.

If thrush is not diagnosed and steps taken to treat it, extensive damage to the horse's foot may occur. In severe cases, the thrush infection may penetrate the horny tissues and involve the sensitive structure of the foot. In such cases, the prognosis is poor. The horse may be lame and the foot may show the same signs of infection that would be encountered in puncture wound of the foot. Adams, O.R., supra at p. 355. Similarly with hoof rot, the hoof rot infection may penetrate the horny tissues and the sheep, goat or cow infected may be lame, joint cavities may be involved, and the animal may show fever and depression, lose weight, and even die. *The Stockman's Handbook*, supra, at p. 378.

It is estimated that hoof thrush affects 5,000,000 horses in the United States alone, and is a constant and significant health problem of horses. It is therefore of great practical importance to be able to provide a method of treating hoof thrush in horses that is fast, simple, effective and humane and which affects a complete cure. It is also of great practical importance to be able to provide a similarly fast, simple and effective method of treating hoof rot in sheep, goats and cattle. Hoof rot is an economically costly disease for commercial raisers of sheep, goats or cattle. Although hoof rot seldom causes death, infected animals generally lose weight and, if lactating, produce less milk. *The Stockman's Handbook*, supra, at p. 379. The disease, therefore, has an adverse economic impact on the costs of meat and milk production. Hoof rot is a highly contagious disease and in sheep, for example, severe outbreaks of hoof rot may affect up to 75% of a flock at one time. Although, as stated above, the mortality rate from hoof rot is low, loss of condition of adult sheep and nursing lambs plus increased labor, equipment and materials to treat the disease make it one of the most costly sheep diseases. *The Sheepman's Production Handbook*, supra, at p. 104.

The present invention is a method which is unexpectedly fast and effective for treating hoof thrush in horses using metronidazole. In mild cases of hoof thrush disease, treatment with metronidazole affected a cure within 24 hours. In the most severe and stubborn cases, treatment with metronidazole affected a cure in less than 21 days. The method should be equally effective in the treatment of the analogous disease of hoof rot in sheep, goats and cattle.

B. Description of the Prior Art

1. Metronidazole

As disclosed in the Physicians Desk Reference, 41st Edition, 1987 (hereinafter, the "PDR"), metronidazole (1-(2-hydroxyethyl)-2-methyl-5-nitroimidazole) is a synthetic antiprotozoal and antibacterial agent well-known for its use as a therapeutic agent in humans. It is marketed as a human pharmaceutical in the United States generically as Metronidazole (Elkins-Sinn, Barr, Danbury, Lederle, Zenith), and also under the following trade names: Flagyl ® (Searle), Metric 21 ® (Fielding), Metryl ® (Lemmon), Protostat ® (Ortho Pharmaceutical) and Satric ® (Savage).

As disclosed in the PDR, metronidazole is particularly well-known as an antiprotozoal therapeutic agent in humans for the treatment of trichomoniasis and amebiasis. In addition, metronidazole has been found to be active in vitro against certain obligate anaerobic bacteria but has not been found to possess clinically relevant activity against facultative anaerobic bacteria or obligate aerobic bacteria. Specifically, metronidazole has been found to have in vitro and clinical activity against the following human pathogenic bacteria:

(a) anaerobic gram-negative bacilli, including Bacteroides species and Fusobacterium species;

(b) anaerobic gram-positive bacilli, including Clostridium species and susceptible strains of Eubacterium; and (c) anaerobic gram-positive cocci, including Peptococcus species and Peptostreptococcus species.

Thus, metronidazole has been used to treat anaerobic bacterial infections in humans including: intra-abdominal infection, skin and skin structure infections, gynecologic infections, bacterial septicemia, bone and joint infections, central nervous system infections, lower respiratory tract infections and endocarditis.

The PDR discloses that the treatment of humans with metronidazole is principally by oral administration of metronidazole in table form. For serious infections or in conjunction with certain surgical procedures, metronidazole has been administered intravenously in humans. The PDR does not disclose any topical use of metronidazole.

2. Thrush

Common techniques for treating hoof thrush in horses fall into three overlapping areas:

1. Removing the cause of the disease by cleanliness and general improvement in the horse's environment;
2. Returning the hoof and frog of the horse to healthy condition through generally accepted husbandry techniques including: (a) removal of necrotic frog tissue, (b) increased exercise and (d) regular and proper trimming of the foot;
3. Applying one or more of the following compounds or products:
   a. formalin;
   b. tincture of iodine;
   c. elemental iodine and turpentine;
   d. hydrogen peroxide;
   e. antimony trichloride or butter of antimony;
   f. household bleach (sodium hypochlorite);
   g. calomel;
   h. creolin;
   i. carbolic acid;
   j. bichloride of mercury;
   k. copper sulphate powder;
   l. alum; or
   m. a host of topical, proprietary remedies.

However, treatment with the above compounds is not equally effective in all horses. Some horses respond poorly to the above compounds. Others do not respond at all. In addition, many of the above compounds are highly toxic or caustic. Currently, treatment of hoof thrush in horses can be "long, difficult and tedious." Rooney, J. R., *The Lame Horse*, A. S. Barnes & Co. (1977) at p. 143.

3. Hoof Rot

Common techniques for treating hoof rot in sheep, goats and cattle fall into three overlapping areas, similar to those for treating thrush:
1. Removing the cause of the disease by cleanliness and dryness in the animal's environment;
2. Removing the diseased tissue by trimming away the affected part of the hoof according to generally accepted techniques;
3. Applying one or more of the following compounds or products:
   a. Formalin/formaldehyde;
   b. copper naphthenate;
   c. iodophor tincture;
   d. copper sulfate;
   e. 2-hydroxymethyl-2-nitro-1,3-propanediol;
   f. bluestone;
   g. a host of other disinfectants.

The animals generally stand in or walk through a foot bath containing a solution of any of the above-listed disinfectants for treatment. *The Sheepman's Production Handbook*, supra, at p. 105; *The Stockman's Handbook*, supra, at p. 379.

However, treatment with any of the above compounds is not equally effective in all animals and some respond poorly to the above compounds. An additional complication in treating hoof rot is that it is so highly contagious that it can rapidly spread to a majority of animals in a flock or herd. In sheep, for example, a severe outbreak of hoof rot can affect up to 75% of a flock at one time. *The Sheepman's Production Handbook*, supra, at p. 104.

A further complication in treating hoof rot is the problem of reoccurence of the disease. Even when the animal is effectively treated, the disease is likely to reoccur if and when the animal is returned to wet pasture conditions. Wet, muddy, unsanitary conditions provide an excellent environment for the causative organisms, primarily *Spherophorus necrophorus*. *The Sheepman's Production Handbook*, supra, at pp. 104–105.

The following U.S. Patents describe other methods for treating or preventing hoof rot: U.S. Pat. No. 3,821,412 describes a method for controlling or preventing hoof rot by treating the ground, such as pen and pastures where the sheep or cattle spend time, with paraformaldehyde; U.S. Pat. No. 3,961,068 describes a method for the treatment of infections in domestic animals that are caused by *Sphaerophorus necrophorus* particularly, hoof rot in cattle, sheep and goats, by oral administration of ipronidazole (1-methyl-2-isopropyl-5-nitroimidazole) in the animal's feed or drinking water or by parenteral administration of ipronidazole in injections; U.S. Pat. No. 3,984,540 describes a method of treating damaged and/or infected tissue in animals, including hoof rot in cattle and sheep, by administering a therapeutic mixture of antibiotic and catalyst, in which the catalyst is a water solubel alkali metal silicate with magnesium and calcium ions; U.S. Pat. No. 4,061,751 describes a method for treating hoof rot and liver abscesses in ruminant animals by administering a therapeutically effective amount of a 6-substituted, 3-nitroimidazo [1, 2-b]pyridazine compound.

SUMMARY OF THE INVENTION

The object of the present invention is to find a fast, simple, effective and humane method for treating the hoof disease in horses known as thrush and in sheep, goats and cattle known as hoof rot. Thrush is a disease of the hoof and frog tissue of horses, caused by a variety of pathogenic microorganisms, primarily the anaerobic bacterium *Spherophorus necrophorus*. Hoof rot is the analogous disease of the hoof in sheep, goats and cattle, also primarily caused by *Spherophorus necrophorus*. It has been discovered that metronidazole is unexpectedly effective in the treatment of hoof thrush in horses.

The present invention encompasses a novel method of treating hoof thrush in horses or hoof rot in sheep and cattle, comprising topically administering a therapeutically effective amount of metronidazole in a carrier to the thrush or hoof rot infected area. Typically, the metronidazole is applied directly on the thrush or hoof rot infected area in the form of a solution, gel, salve or ointment for a treatment period effective to cure the thrush or hoof rot infection. Preferably, the metronidazole is applied directly to the thrush or hoof rot infected area in the form of a solution.

DETAILED DESCRIPTION

The present invention is directed to a new and improved method for treating hoof thrush in horses or in other equine animals susceptible to hoof thrush disease and for treating hoof rot in sheep, goats and cattle. By "equine animals" is meant a horse, donkey, mule, burro or zebra. However, the preferred animal is a horse. Hereinafter, the term "horse" encompasses all equine animals.

By hoof thrus is meant a disease in horses of the hoof and frog tissue caused by a variety of pathogenic microorganisms, primarily the anaerobic bacterium *Spherophorus necrophorus*. By hoof rot is meant an analogous disease of the hoof in sheep, goats and cattle, also primarily caused by *Spherophorus necrophorus*. The diagnostic signs of thrush disease or hoof rot include a strong unpleasant odor and discharge from the frog tissue. A veterinarian of ordinary skill can readily determine whether a horse exhibits a thrush infection or whether a sheep, goat or cow exhibits a hoof rot infection.

In particular, the present invention relates to a method for treating thrush (in a horse) or hoof rot (in a sheep, goat or cow) comprising topically administering a therapeutically effective amount of metronidazole in a carrier directly on a thrush or hoof rot infected area for a treatment period effective to cure the thrush or hoof rot infection.

The present invention encompasses a method for the administration of metronidazole topically, at and near the thrush or hoof rot infected area, in the form of a solution or in the form of a gel, salve or ointment.

For topical administration in the form of a solution, the active drug component of the present invention, metronidazole, in liquid, powdered or lyophilized form may be combined with a suitable pharmaceutical diluent or carrier (collectively referred to herein as "carrier" materials) such as water, saline, aqueous buffers, and the like. The method of application of the metronidazole in the form of a solution may be by pouring, squirting, flushing or sponging the metronidazole solution on the thrush or hoof rot infected area. In a preferred embodiment for treating thrush, a disposable plastic syringe (without a needle) may be filled with some of the metronidazole solution for treatment and squirted on the thrush infected area. Alternatively, the horse's hoof may be submerged or immersed or soaked in the metronidazole solution to effect the treatment. (For example, Horses 23 adn 41 in Table 1). In severe case, such a soaking treatment may be necessary to effectively cure the thrush. (For example, Horse 22 in Table 1). In a preferred embodiment for treating hoof rot, the sheep, goat or cow is walked through a foot bath containing the metronidazole solution.

For topical administration in the form of a gel, salve or ointment, the metronidazole as above may be combined with a suitable carrier such as Aquaphor® (Biersdorf Corp., Hartford, Conn.). The method of application of the metronidazole in the form of a gel, salve or ointment may be by contacting and rubbing the gel, salve or ointment on, in, around and throughout the thrush or hoof rot infected areas of the animal's hoof and frog.

Regardless of the form and method of administration selected (e.g. solution, gel, salve, ointment), the metronidazole is formulated into pharmaceutically acceptable dosage forms by conventional methods known to those skilled in the art.

Regardless of the form and method of administration selected, a non-toxic but therapeutically effective amount of metronidazole is employed in any treatment. The dosage regimen for treating hoof thrush or hoof rot with metronidazole is selected in accordance with a variety of factors, including the medical condition of the animal, the severity of the infection and the form of administration. A veterinarian of ordinary skill can readily determine and prescribe the effective amount of metronidazole required to cure the thrush or hoof rot infection. In so proceeding, the veterinarian could employ relatively low doses at first and subsequently increase the dose until a maximum response is obtained. A therapeutically effective amount is in the range from about 100 mg. to about 1,000 mg. per 100 ml. carrier. The preferred amount is in the range from about 250 mg. to about 750 mg. per 100 ml. carrier. The most preferred amount is about 500 mg. per 100 ml. carrier.

In the present invention, metronidazole has been found to be unexpectedly effective in the treatment of hoof thrush in horses, when administered topically as a solution or as an ointment. Fifty horses of various ages (from 1-17 years old) and breeds (more than 15 different breeds) were treated with metronidazole (Table I). The various breeds represented in Table 1 are representative of 75-80% of the horses in the United States. Each horse had been diagnosed by a veterinarian as having hoof thrush of varying severity. Several horses (for example, Horses 16, 17 and 20) were diagnosed as having chronic thrush. In most horses, all 4 hooves were infected with the disease, but for several horses only 2 hooves were infected (For example, Horse 1, 5, 20 in Table I).

The results from the treatment of this group of 50 thrus-infected horses are presented in Table I. Parameters used to diagnose the presence and severity of the thrush disease in each horse were: (1) a strong, unpleasant odor associated with the infected hoof and frog tissue, (2) a black discharge from the sulcae of the frog tissue, (3) a softening and destruction of the frog tissue, and (4) lameness.

TABLE I

Treatment of Thrush Infected Hooves with Metronidazole

| Horse | Metronidazole (mg/100 ml) | Dates of Treatment* | Latest Date of Cure* |
|---|---|---|---|
| 1 | 250 | 5/30, 6/3, 6/5, 6/8 | 6/10 |
| 2 | 500 | 6/20, 6/22, 6/25 6/27 (LH) | 6/27 (2F, RH) 6/29 (LH) |
| 3 | 500 | 6/10, 6/12, 6/15 | 6/15 |
| 4 | 500 | 6/3, 6/5, 6/7, 6/9, 6/11 6/14 | 6/14 |
| 5 | 250 | 6/5, 6/7, 6/10, 6/12 | 6/12 |
| 6 | 500 | 6/1, 6/4, 6/7 (2H), 6/10 (2H), 6/12 (2H) | 6/7 (2F), 6/12 (2H) |
| 7 | 500 | 6/3, 6/6, 6/9, 6/12, 6/15 (2H), 6/17 (2H) | 6/12 (2F), 6/17 (2H) |
| 8 and 9 | 500 | 6/3, 6/6, 6/9, 6/12 | 6/12 |
| 10 | 500 | 6/3, 6/6, 6/9 | 6/9 |
| 11 | 500 | 7/8, 7/10, 7/12, 7/14 (2H), 7/18 (2H) | 7/14 (2F), 7/18 (2H) |
| 12 | 500 | 4/10, 4/14 4/17 (RH) | 4/14 (2F, LH), 4/17 (RH) |
| 13 | 250 | 4/13, 4/15, 4/18 (RH) | 4/18 (2F, LH), 4/20 (RH) |
| 14 | 500 | 4/15, 4/17, 4/19, 4/23, 4/25 | 4/25 |
| 15 | 250 | 7/23, 7/25, 7/27 7/29 | 7/27 (2F), 7/29 (2H) |
| 16 | 500 | 6/1, 6/3, 6/5, 6/10 (RF, RH) | 6/5 (LF, LH), 6/10 (RF, RH) |
| 17 | 500 | 6/1, 6/2, 6/3, 6/4, 6/5 | 6/5 |
| 18 | 500 | 5/30, 6/1 | 6/3 |
| 19 | 500 | 5/30, 6/1, 6/3 | 6/5 |
| 20 | 250 | 6/1, 6/2, 6/3, 6/4 (2H) | 6/4 (2F), 6/7 (2H) |
| 21 | 250 | 6/2, 6/3, 6/10 (2F) | 6/3 (2H), 6/10 (2F) |
| 22 | 500 | 8/1, 8/3, 8/10, 8/11, 8/14, 8/17 (2H), 8/20 (2H) | 8/17 (2F), 8/20 (2H) |
| 23 | 500 | 8/16, 8/17, 8/20, 8/24, 8/28, 8/30, 9/3 | 9/3 |
| 24 | 500 | 5/30, 6/2, 6/7, 6/10 | 6/10 |
| 25 | 250 | 6/1, 6/3, 6/5 | 6/5 |

TABLE I-continued
Treatment of Thrush Infected Hooves with Metronidazole

| Horse | Metronidazole (mg/100 ml) | Dates of Treatment* | Latest Date of Cure* |
|---|---|---|---|
| 26 | 250 | 5/20, 5/22, 5/24, 5/26 | 5/26 |
| 27 | 250 | 5/4, 5/6, 5/8 | 5/8 |
| 28 | 250 | 5/26, 5/28, 5/30 | 5/30 |
| 29 | 500 | 5/20, 5/22, 5/24, 5/26 | 5/26 |
| 30 | 250 | 4/6, 4/8, 4/10, 4/12 | 4/12 |
| 31 | 250 | 4/10, 4/12, 4/15 | 4/15 |
| 32 | 250 | 8/15, 8/18, 8/20 | 8/20 |
| 33 | 500 | 6/3, 6/5, 6/7, 6/9 | 6/7 |
| 34 | 500 | 6/3, 6/5, 6/7, 6/9 | 6/9 |
| 35 | 500 | 5/10, 5/12, 5/15, 5/17 | 5/17 |
| 36 | 500 | 5/10, 5/12, 5/15, 5/17 | 5/17 |
| 37 | 500 | 4/21, 4/23, 4/25, 4/27 (2H), 4/29 (2H) | 4/27 (2F), 4/29 (2H) |
| 38 | 250 | 5/26, 5/28, 5/30 | 5/30 |
| 39 | 250 | 6/2, 6/4, 6/6 | 6/6 |
| 40 | 250 | 4/20, 4/22, 4/24 | 4/24 |
| 41 | 250 | 6/2, 6/4, 6/6, 6/8 | 6/8 (2F), 6/10 (2H) |
| 42 | 500 | 5/25, 5/27, 5/30 | 5/30 |
| 43 | 500 | 6/2, 6/5, 6/7 | 6/7 |
| 44 | 500 | 4/22, 4/24, 4/26 | 4/26 |
| 45 | 500 | 5/3, 5/5, 5/7 | 5/7 |
| 46 | 500 | 4/26, 4/28, 4/30, 5/2 (2H), 5/5 (2H) | 5/2 (2F), 5/5 (2H) |
| 47 | 250 | 5/15, 5/17, 5/19, 5/21 (2H), 5/23 (2H), 5/25 (2H) | 5/21 (2F), 5/25 (2H) |
| 48 | 250 | 4/20, 4/23, 4/25 | 4/25 |
| 49 | 250 | 5/16, 5/18, 5/20 | 5/20 |
| 50 | 250 | 6/12, 6/15, 6/17 | 6/17 |

*F refers to fore hoof; H refers to hind hoof; LH refers to left hind hoof; RH refers to right hind hoof.

In Table I, the parameters used to measure effective treatment and cure consisted of the following: (1) odor associated with hoof and frog tissue (2) dryness of bulbs of heal and frog and no discharge, (3) examination of frog tissue and (4) ability to walk without lameness. With respect to the examination of frog tissue, a physical examination by a veterinarian was made of the frog tissue of each of the horses treated as summarized in Table 1. In addition, for 10 of the horses listed in Table I, a histological examination was made of the frog tissue. Tissue samples were taken after treatment had been completed and tested for the presence of the causative agents of thrus, in particular, anaerobic bacteria. The histological results for these 10 horses showed that no anaerobic bacteria could be cultured from frog tissue that was treated with metronidazole to cure the thrush.

Without exception, each of the horses treated according to the method that is the present invention was effectively cured of thrush. This included Horse 22, which had been treated for an entire year with formalin without any success in effecting a cure of the thrush infection, prior to the time of treatment with metronidazole according to the present invention. This also included several other horses (Horses 16 and 17), that like Horse 22 were diagnosed as having chronic thrush. In no case did a horse require treatment for more than 20 days (the most severe case) and in a majority of cases, a cure was affected within 7 days of treatment. In fact, in another group of 20 horses not include in Table I, all 20 horses were effectively cured of thrush within 3 days of treatment.

The above-described data clearly show that metronidazole is unexpectedly fast and effective in curing thrush. Further, metronidazole treatment conferred protection against recurrence of thrush infection. The 70 horses treated with metronidazole with the results reported herein have been observed over a period of a year since treatment. In general, no recurrence has been observed within this one-year period. This result was totally unexpected and has never been demonstrated with any other prior method of treating thrush. The mechanism by which metronidazole treatment confers protection against recurrence of thrush infections is not well-understood at this time. Nevertheless, these data clearly demonstrate two unexpected results: (1) that topical administration of metronidazole is unexpectedly effective in treating thrush, and (2) that topical administration of metronidazole is unexpectedly effective in preventing recurrence of thrush.

The following examples further illustrate the invention:

EXAMPLE 1

Treatment of Thrush Infected Hooves Using Metronidazole Solution

A. Preparation of Metronidazole Solution

Each metronidazole solution used in treatment was prepared by a registered pharmacist as follows: metronidazole powder of pharmaceutical grade U.S.P. XXI (Farchemia SPA, Milan Italy) was solubilized and diluted in sterile distilled water. Either 250 mg. or 500 mg. of the metronidazole powder was mixed with 100 ml. of the water to yield a 2.5 mg/ml. or a 5.0 mg/ml metronidazole solution. The solutions were routinely used within 60 days of their preparation but have an estimated shelf life of at least 2 years.

B. Treatment Procedure

1. Flushing

In general, each hoof to be treated was cleaned with a hoof pick. The pick was used to remove material in and around the frog and heel. In some cases, the hooves were not preliminarily cleaned with a hoof pick, but treated directly with the metronidazole solution. To apply the metronidazole solution to the pick-cleaned (or uncleaned) hoof, a disposable sterile plastic syringe without a needle was filled with approximately 10 cc. of the metronidazole solution prepared as in Part A of this Example, and the solution was squirted on the thrush infected area in order to flush the entire infected area. Only one such flushing was performed per hoof per day of treatment.

2. Soaking

Several horses, for example, Horses 22, 23 and 41 in Table I were treated on some days of treatment by soaking the hooves in a metronidazole solution. Each hoof was submerged and immersed in a 2.5 mg/ml. or 5.0 mg/ml. metronidazole solution prepared as in Part A of this Example. In general, a bucket was filled with approximately 1 pint of the metronidazole solution. Each thrush infected hoof, after it was cleaned with a hoof pick according to paragraph 1 of this Part B, was placed in the bucket containing the solution and was completely submerged and soaked in the solution for approximately 2 minutes. The time of soaking ranged from approximately 30 seconds to 2 minutes.

EXAMPLE 2

Treatment of Thrush Infected Hooves Using Metronidazole Ointment

A. Preparation of Metronidazole Ointment

Metronidazole ointment was prepared by a registered pharmacist as follows: 100 mg. of metronidazole powder as in Example 1 was mixed directly with 30 g. Aquaphor ® gel to yield a metronidazole ointment.

B. Treatment Procedure

Preliminarily, each hoof to be treated was cleaned with a hoof pick as described in Example 1. The pick-cleaned hoof was lifted and held while the metronidazole ointment was rubbed on, in, around and throughout the thrush infected areas of the hoof and frog tissue, including the sulcae of the frog tissue. The metronidazole ointment was sometimes applied using a brush to insure that the ointment gets into all clefts and crevices of the heel and frog tissue. The treated hoof may be left exposed or may be covered with paper to protect the treated hoof. A paper covering of the hoof was prepared as follows. The shape of the hoof was traced onto a brown paper bag. The paper was then cut to the shape of the hoof and shoe. The paper was trimmed to fit inside the hoof and was tucked under the shoe, where it remained as a protective cover for the treated hoof.

EXAMPLE 3

Treatment of Hoof Rot Infected Hooves Using Metronidazole Solution

A. Preparation of the Foot Bath

The metronidazole solution is prepared according to Part A of Example 1, except that at least 25-30 gallons of a 2.5 mg/ml or 5.0 mg/ml solution is prepared instead of 100 ml. of such solution. At least 25-30 gallons of such a solution is poured into a foot bath to yield a solution in the foot bath that is 2-3 inches deep so as to allow immersion of the animal's hoof up to the coronet band or hairline. The dimensions of the foot bath should be such that it takes 15-30 seconds for the animal to walk through the foot bath.

B. Treatment Procedure

Preliminarily, each hoof to be treated may be (but need not be) cleaned with a hoof pick to remove packed material in and around the frog and heel. Each sheep, goat or cow to be treated is then walked through a foot bath prepared according to Part A of this Example. The period of each treatment should be at least 15-30 seconds.

What is claimed is:

1. A method of treating hoof thrush in a horse or hoof rot in a sheep, goat or cow comprising topically administering a therapeutically effective amount of metronidazole in a carrier directly on a thrush or hoof rot infected area for a treatment period effective to cure the thrush or hoof rot infection.

2. The method according to claim 1 wherein the treatment period is from about one to about 30 days.

3. The method according to claim 2 wherein the therapeutically effective amount of metronidazole is topically administered in the form of a solution.

4. The method according to claim 3 wherein the therapeutically effective amount of metronidazole comprises about 100 mg. to about 1000 mg metronidazole per 100 ml. of the carrier.

5. The method according to claim 4 wherein the therapeutically effective amount of metronidazole comprises from about 250 mg. to about 750 mg. metronidazole per 100 ml. of the carrier.

6. A method according to claim 5 wherein the therapeutically effective amount of metronidazole comprises about 500 mg. metronidazole in 100 ml of the carrier.

7. The method according to claim 2, wherein the therapeutically effective amount of metronidazole is topically administered in the form of a gel, salve or ointment.

8. The method according to claim 7 wherein the therapeutically effective amount of metronidazole comprises from about 100 mg. to about 1000 mg. metronidazole per 30 g. of the carrier.

9. The method according to claim 8 wherein therapeutically effective amount of metronidazole comprises from about 250 mg. to about 750 mg. metronidazole per 30 g. of the carrier.

10. The method according to claim 9 wherein the therapeutically effective amount of metronidazole comprises about 500 mg. metronidazole per 30 g. of the carrier.

11. A method according to claim 2, wherein the therapeutically effective amount of metronidazole is administered one or more times during the treatment period.

12. A method according to claim 11 wherein the therapeutically effective amount of metronidazole is administered one time per day during the treatment period.

13. A method according to claim 11 wherein the therapeutically effective amount of metronidazole is administered one time about every two to four days during the treatment period.

* * * * *